(12) United States Patent
McDonald et al.

(10) Patent No.: US 7,030,060 B1
(45) Date of Patent: Apr. 18, 2006

(54) REST-BREAKING COMPOSITION AND USE THEREOF

(75) Inventors: Brian P. McDonald, Lochem (NL); Hennie A. Workel, Enschede (NL)

(73) Assignee: Akzo Nobel N.V., Arnhen (NL)

( * ) Notice: Subject to any disclaimer, the term of this patent is extended or adjusted under 35 U.S.C. 154(b) by 162 days.

(21) Appl. No.: 10/031,225

(22) PCT Filed: Jul. 3, 2000

(86) PCT No.: PCT/EP00/06234

§ 371 (c)(1),
(2), (4) Date: Jun. 5, 2002

(87) PCT Pub. No.: WO01/05227

PCT Pub. Date: Jan. 25, 2001

(30) Foreign Application Priority Data

Jul. 16, 1999 (EP) .................................. 99202342

(51) Int. Cl.
*A01N 25/30* (2006.01)
*A01N 33/08* (2006.01)
*A01N 33/12* (2006.01)
*A01N 59/24* (2006.01)

(52) U.S. Cl. .................. 504/116; 504/188; 504/354

(58) Field of Classification Search ............... 504/116, 504/188, 354, 254
See application file for complete search history.

(56) References Cited

U.S. PATENT DOCUMENTS

| | | | |
|---|---|---|---|
| 4,125,393 A | 11/1978 | Kohl et al. | 71/3 |
| 4,309,205 A | 1/1982 | Kessler | 71/27 |
| 5,658,855 A | 8/1997 | Nalewaja et al. | 504/214 |
| 5,693,591 A * | 12/1997 | North et al. | 504/365 |
| 5,885,932 A * | 3/1999 | Parr et al. | 504/116.1 |
| 6,518,221 B1 * | 2/2003 | Schulteis | 504/121 |

FOREIGN PATENT DOCUMENTS

| | | |
|---|---|---|
| GB | 2059412 A | 4/1981 |
| WO | WO 94/23574 | 10/1994 |
| WO | WO 96/01049 | 1/1996 |
| WO | WO 97/24926 | 7/1997 |

OTHER PUBLICATIONS

*Winter Dormancy and Delayed Foliation*, The Deciduous Fruit Grower. Blommaert (Winterrustyd en vertraagde Bot), (1956), pp. 77, 83 and English translation.
*Surfactants Europa, A Directory of Surface Active Agents available in Europe*, The Royal Society of Chemistry, Cambridge (1995) Hollis.
Kirk-Othmer *Encyclopedia of Chemical Technology*, Third Edition, vol. 10, John Wiley & Sons (1980) pp. 47-56.
International Search Report, dated: Nov. 18, 1999 for EP 99 20 2342.

* cited by examiner

*Primary Examiner*—Sabiha Qazi
(74) *Attorney, Agent, or Firm*—Ralph J. Mancini; Michelle J. Burke

(57) ABSTRACT

The invention relates to a composition useful for the breaking of rest in deciduous fruit species such as apple species and grape species comprising an organic nitrogen-containing compound having a molecular weight of 60 to 300 with the exception of urea and dinitro-ortho-cresol, an inorganic nitrate rest-breaking agent, and a surfactant. Preferably, the organic nitrogen-containing compound is a choline salt such as choline chloride, the inorganic nitrate rest-breaking agent is selected from the group consisting of potassium nitrate, calcium nitrate, ammonium nitrate, calcium ammonium nitrate, urea ammonium nitrate, zinc ammonium nitrate, and mixtures thereof, and the surfactant is an alkoxylated amine such as Armoblen ®*, and Berol®* compound or an alkoxylated quaternary ammonium compound.

17 Claims, No Drawings

REST-BREAKING COMPOSITION AND USE THEREOF

The present application was filed on Jul. 3, 2000 as application serial number PCT/EP00/06234 and claims priority of European patent application No. 99202342.4 filed on Jul. 16, 1999.

The invention relates to a rest-breaking composition and the use thereof.

Deciduous fruit species require winter chilling to grow normally. The amount of chilling required depends upon the kind of fruit and the cultivar. If winter chilling is insufficient, then growth abnormalities such as delayed and uneven blossoming, poor leaf cover, insufficient fruit set, and reduced fruit size can occur. These symptoms are generally referred to as delayed foliation.

Measures to reduce the symptoms of delayed foliation include treatment with rest-breaking agents during later winter and various physical manipulations such as pruning. In South Africa, for example, most apple trees receive insufficient winter chilling to break rest completely and thus annual application of a rest-breaking agent is standard practice.

The most widely used rest-breaking agents are dinitro-ortho-cresol (DNOC) in combination with oil and hydrogen cyanamide in combination with oil (e.g. Dormex sold by SKW Trostberg). The oil in these compositions is used to allow an even distribution of the agent over the species to be treated. It is to be noted that although DNOC/oil and hydrogen cyanamide/oil compositions are effective at breaking rest in deciduous fruit species, DNOC is harmful to the environment and its use is prohibited in Europe and the United States, and hydrogen cyanamide is toxic to man, limiting its use in certain rest-breaking applications.

Another known rest-breaking agent is potassium nitrate, which has been shown to have a positive effect on peach species. However, potassium nitrate is not as effective as DNOC or hydrogen cyanamide. It is to be noted that deciduous fruit species with a high chill requirement, such as grape species, require a relatively high concentration of such a rest-breaking agent.

WO 94/23574 describes additives which promote the activity of rest-breaking agents such as hydrogen cyanamide and potassium nitrate. These additives, i.e., surfactants which are also referred to as (tank mix) adjuvants, are alkoxylated amines (e.g. Armoblen®, sold by Akzo Nobel) and alkoxylated quaternary ammonium compounds.

WO 96/01049 and WO 97/24926 describes the use of the aforementioned types of additives (additionally disclosing the use of Armobreak®, sold by Akzo Nobel) in combination with hydrogen cyanamide and several inorganic nitrate rest-breaking agents, i.e., potassium nitrate, ammonium nitrate, calcium nitrate, urea ammonium nitrate, calcium ammonium nitrate, and zinc ammonium nitrate, and mixtures thereof.

Although the compositions described in the aforementioned international patent publications effectively break the rest in various deciduous fruit species, they do not reach the desired level of uniformity of bud break, nor the desired balance of vegetative and reproductive bud break.

GB-A-2 059 412 describes the application of an aqueous solution of a choline salt to enhance the reproductive development of plants including deciduous fruit trees such as apple, pear, plum, and peach trees. It is described that treatment of deciduous fruit trees results in break of dormancy.

However, as is shown in the Examples of the present patent application, the use of only a choline salt in combination with a surfactant does not give the desired rest-breaking activity either.

For the foregoing reasons, there is still a need in the art for improved rest-breaking compositions which are effective, less toxic than the most-effective compositions that are known in the art of rest-breaking, which can be employed at economically and environmentally acceptable concentrations of the active ingredients, and which are non-hazardous to operators of the application equipment.

The present invention relates to a composition useful for the breaking of rest in deciduous fruit species comprising an organic nitrogen-containing compound having a molecular weight of 60 to 300 with the exception of urea and dinitro-ortho-cresol, an inorganic nitrate rest-breaking agent, and a surfactant.

The use of the composition of the present invention for breaking the rest of deciduous fruit species produces improvements in advancing the time of bloom, bud break and/or leaf cover and fruit set, leading to an improved quality of the fruit.

In Table 1 of the present application, the percentage of overall bud break is presented as a representative parameter for evaluating the rest-breaking activity of a given composition.

In the context of the present invention, by the term "deciduous fruit species" is meant any species which requires the use of a rest-breaking agent due to delayed foliation, in order to improve the yield and quality of the fruit in regions which have mild winter weather conditions. Besides the term rest-breaking agent, the terms dormancy-breaking agent and bud-breaking agent are also used frequently in this field of technology. Typical examples of deciduous fruit species include species bearing apples, pears, peaches, apricots, plums, cherries, grapes, vines, kiwis, nectarines, or almonds. The rest-breaking composition of the present invention is particularly suitable for use on apple species and grape species.

Preferably, the organic nitrogen-containing compound has a molecular weight of 60 to 250, more preferably 60 to 200, and most preferably 60 to 150.

Urea and dinitro-ortho-cresol have been excluded from protection, because urea may be added to the composition of the invention in the form of urea ammonium nitrate and dinitro-ortho-cresol is undesired due to the fact that it is harmful to the environment.

Typical examples of organic nitrogen-containing compounds in accordance with the present invention include ethylenediamine, ($C_1$–$C_3$)alkylated ethylene-diamines such as N-methyl-ethylenediamine and N,N-diethylethylenediamine, ethanolamine, ($C_1$–$C_3$)alkylated ethanolamines such as N-methylethanolamine and N,N-diethylethanolamine, (carboxymethyl)tri-($C_1$–$C_3$)alkylammonium salts such as (carboxymethyl)trimethylammonium hydroxide inner salts or betaine and 1-carboxy-N,N,N-trimethanaminium chloride or betaine hydrochloride, (2-hydroxyethyl)tri($C_1$–$C_3$) alkylammonium salts such as (2-hydroxyethyl)trimethylammonium or choline choloride, (2-hydroxypropyl)tri ($C_1$–$C_3$)alkylammonium salts, (2-hydroxybutyl)tri($C_1$–$C_3$) alkylammonium salts, and mixtures thereof. The $C_1$–$C_3$-alkyl group preferably is a methyl or ethyl group, most preferably a methyl group. The term salt in the aforementioned classes of compounds is well known to the person skilled in the art and it typically refers to salts containing a halide ion such as a chloride ion or a (methyl)sulfate ion.

Preferably, the organic nitrogen-containing compound is selected from the group consisting of (2-hydroxyethyl)tri($C_1$–$C_3$)alkylammonium salts, (2-hydroxypropyl)tri($C_1$–$C_3$) alkylammonium salts, and (2-hydroxybutyl)tri($C_1$–$C_3$)-alkylammonium salts, and mixtures thereof. More preferably, it is a (2-hydroxyethyl)trimethylammonium or choline salt. Most preferably, it is choline choloride.

Typical examples of choline salts which can be used in the composition of the invention include choline chloride, choline nitrate, choline phosphate, choline sulfate, choline bitartrate, choline dihydrogen citrate, tricholine citrate, choline bicarbonate, choline carbonate, and mixtures thereof.

It is to be understood that not all compounds may work on all deciduous fruit species in all orchards. For example, it was found that choline borate could not be used on Golden Delicious apples in South Africa. By routine experimentation one of ordinary skill in the art can establish, however, which compounds produce the desired rest-breaking effect and which do not.

Typical examples of inorganic nitrate rest-breaking agents or nitrogen fertilizers which can be used in the composition of the invention include alkali metal and earth alkali metal nitrates such as sodium nitrate, potassium nitrate, and calcium nitrate, ammonium nitrates such as ammonium nitrate itself, calcium ammonium nitrate, urea ammonium nitrate, and zinc ammonium nitrate, and mixtures thereof. Preferably, the inorganic nitrate rest-breaking agent is selected from the group consisting of potassium nitrate, calcium nitrate, ammonium nitrate, calcium ammonium nitrate, urea ammonium nitrate, zinc ammonium nitrate, and mixtures thereof. The use of calcium nitrate, calcium ammonium nitrate, urea ammonium nitrate, and mixtures thereof is particularly preferred.

In the context of the present invention, by the term "surfactant" is meant any compound which improves the distribution of the organic nitrogen-containing compound and the inorganic nitrate rest-breaking agent over the deciduous fruit species to be treated. Hence, oils such as those which have been used in combination with dinitro-ortho-cresol and hydrogen cyanamide, are also meant to be included in this term. As is known to the person skilled in the art, surfactants are typically classified as amphoterics, anionics, cationics, nonionics, and miscellaneous surfactants. It was found that, as is known in the art, the type of surfactant used is not critical. Any of the known types of surfactants may be used in the composition in accordance with the present invention, as long as they achieve an even distribution of the ingredients of the invention composition over the deciduous fruit species to be treated. By routine experimentation one of ordinary skill in the art can establish which surfactants work, which do not, and which work best.

The alkoxylated amine surfactants and alkoxylated quaternary ammonium surfactants which are described in WO 94/23574 (i.e. on page 4, line 12, through page 8, line 17, and on page 12, lines 1–11), WO 96/01049 (i.e. on page 4, line 13, through page 8, line 10, and on page 12, lines 12–24) and WO 97/24926 (i.e. on page 4, line 24, through page 10, line 2) are particularly preferred for use in the invention composition. More preferably, an alkoxylated amine is used. Most preferably, Armoblen®, Armobreak®, and Berol® compounds, which are commercially available from Akzo Nobel Chemicals, are used in the invention composition.

In a preferred embodiment, the composition in accordance with the present invention comprises an organic nitrogen-containing compound selected from choline salts, an inorganic nitrate rest-breaking agent selected from potassium nitrate, calcium nitrate, ammonium nitrate, calcium ammonium nitrate, urea ammonium nitrate, zinc ammonium nitrate, and mixtures thereof, and a surfactant selected from alkoxylated amines.

The composition of the present invention is typically applied to the deciduous fruit species prior to blossom. The optimum time to break rest for a particular deciduous fruit species will depend upon several factors includng the type of fruit, the cultivar, the climatic conditions, and the types and amounts of the rest-breaking agents being applied. For some fruit or cultivar species, the best rest-breaking effects are accomplished by early application of the rest-breaking composition, whereas for others it is best to wait until just before blossom. In general, the rest-breaking composition will be applied at some point between the time when winter has peaked and the time when blossoming begins.

The rest-breaking composition in accordance with the present invention is preferably applied in the form of an aqueous solution. As is known to the person skilled in the art, the invention compositions may be prepared on site by the end user shortly before application to the deciduous fruit species to be treated, and are referred to as tank-mix compositions, or alternatively may be provided to the end user already formulated, either at the desired dilution for application (i.e. ready-to-use compositions) or requiring dilution, dispersion or dissolution in water by the end-user (i.e. concentrate compositions). Such preformulated compositions are storage stable and may be liquid or dry.

The amounts of the organic nitrogen-containing compound and the inorganic nitrate rest-breaking agent to be used in the composition for breaking the rest of deciduous fruit species are dependent on a number of parameters including the deciduous fruit species and cultivar to be treated, the type of organic nitrogen-containing compound and inorganic nitrate rest-breaking agent used, the volume of the aqueous solution per hectare, the required total amount of nitrogen per hectare, the application equipment used, and the design of the orchard. For example, for the treatment of apple trees typically a volume of 1,500 liters per hectare is used, whereas for grape species only a volume of 150 liters per hectare is employed. By routine experimentation and with the guidance of the data provided in the Examples one of ordinary skill in the art can establish which amounts need to be used in any given situation.

The amount of surfactant in the ready-to-use aqueous solution typically is in the range of 0.1 to 10% by volume, preferably 1 to 10% by volume, more preferably 1 to 5% by volume, based on the total volume of the composition.

The composition of the invention is preferably applied in a manner similar to that in which commercial crop protection products and nutrients are applied.

More particularly, conventional equipment such as knapsack sprayers, hand-held spray guns, mist blowers, and aerial spraying equipment among others may be used. The compositions may also be applied directly to the plant by hand, if desired.

The use of the composition of the present invention has the following significant advantages: it breaks rest to the extent that the use of known, highly toxic rest-breaking agents can be eliminated, in a manner which is safe for the crops and without the treatment having any long-term phytotoxic effect on the plants, if carried out correctly. Further, its use will cause significantly less harm to beneficial insects when applied within the normal application volume, and its use appears to be environmentally acceptable, non-hazardous to operators of the application equipment, and non-corrosive to the equipment.

The present invention also relates to the use of the composition which has been described above for breaking the rest in deciduous fruit species, in particular in the case of apple species and grape species.

The present invention is illustrated by the following examples.

Comparative Examples A–D and Example 1

In these examples, five rest-breaking compositions in which the amounts of the ingredients present are expressed as volume percentage were applied to Golden Delicious apple trees in the course of 1998 in Somerset West, Cape Province, Republic of South Africa. The percentage of overall bud break was determined at two dates, i.e. Oct. 5, 1998, at about the start of bud break, and Oct. 26, 1998, at about the end of bud break. The results are depicted in Table 1. The higher this percentage, the better the rest-breaking effect of the composition.

With the compositions of Comparative Examples C and D and Example 1, 1.02 kg nitrogen equivalents/hectare of apple trees were distributed, the spray volume was about 1,500 liters/hectare.

TABLE 1

Effect of rest-breaking compositions on % overall bud break

| Example | Composition (vol %) | Bud break (%) Start | end |
|---|---|---|---|
| A | 6% DNOC/oil | 17 | 52 |
| B | 0.5% Dormex, 2% BP oil | 13 | 36 |
| C | 1.5% Acer907s98, 6% GAN | 12 | 26 |
| D | 1.5% Acer907s98, 13% AcerCC98 | 22 | 38 |
| 1 | 1.5% Acer907s98, 6.6% AcerCC98, 3% GAN | 38 | 60 |

DNOC is dinitro-ortho-cresol formulated in oil
Dormex is hydrogen cyanamide
Acer907s98 or Berol® 907 is an alkoxylated amine surfactant
GAN is a mixture of an aqueous calcium nitrate solution and an aqueous urea ammonium nitrate solution in a volume ratio of approximately 2:1
AcerCC98 is choline chloride (75 wt % aqueous solution)

DNOC is dinitro-ortho-cresol formulated in oil

Dormex is hydrogen cyanamide

Acer907s98 or Berol®907 is an alkoxylated amine surfactant

GAN is a mixture of an aqueous calcium nitrate solution and an aqueous urea ammonium nitrate solution in a volume ratio of approximately 2:1

AcerCC98 is choline chloride (75 wt % aqueous solution)

The results in Table 1 indicate the synergistic effect of the combination of choline chloride, i.e. an organic nitrogen-containing compound, a mixture of calcium nitrate and urea ammonium nitrate, i.e. inorganic nitrate rest-breaking agents, and an alkoxylated amine, i.e. a surfactant, and the improvement over the rest-breaking compositions DNOC/oil and hydrogen cyanamide/oil of the prior art.

It was observed that, unlike the compositions of the prior art, the composition of Example 1 showed 100% terminal bud break. Furthermore, the invention composition showed an improved balance of reproductive versus vegetative bud break over the compositions of the prior art.

Comparative Examples E–F and Example 2

Table 2 lists the results of a rest-breaking trial on Golden Delicious apples trees in the course of the 1999–2000 growth season in the Western Cap of South Africa. Average fruit per cm stem diameter is a known measure for the fruit yield. Average fruit diameter in mm is a known measure for the quality of the fruit.

TABLE 2

Effect of rest-breaking compositions on fruit yield and quality

| Example | Composition (vol %) | Average fruit per cm stem diameter | Average fruit diameter in mm |
|---|---|---|---|
| E | 6% DNOC/oil | 23.1 | 25.8 |
| F | 0.5% Dormex, 3% oil | 26.3 | 26.5 |
| 2 | 1.5% Acer 907s98, 3.3% AcerCC98, 4.5% GAN | 26.3 | 27.3 |

See the notes to Table 1.

The results in Table 2 indicate that as a result of using a rest-breaking composition in accordance with the present invention, fruit having a higher quality was obtained as compared to using a composition of the prior art.

The invention claimed is:

1. A composition useful for the breaking of rest in deciduous fruit species comprising an organic nitrogen-containing compound selected from the group consisting of ethylenediamine, ($C_1$–$C_3$)alkylated ethylenediamines, (carboxymethyl)tri-($C_1$–$C_3$)-alkylammonium salts, (2-hydroxyethyl)tri($C_1$–$C_3$)alkylammonium or choline salts, (2-hydroxypropyl)tri($C_1$–$C_3$)alkylammonium salts, (2-hydroxybutyl) tri($C_1$–$C_3$)alkylammonium salts, and mixtures thereof, an inorganic nitrate rest-breaking agent, and a surfactant.

2. The composition of claim 1 wherein the organic nitrogen-containing compound is selected from the group consisting of (2-hydroxyethyl)tri($C_1$–$C_3$)alkylammonium salts, (2-hydroxypropyl)tri($C_1$–$C_3$)alkylammonium salts, and (2-hydroxybutyl)tri($C_1$–$C_3$)-alkylammonium salts, and mixtures thereof.

3. The composition of claim 2 wherein the organic nitrogen-containing compound is a (2-hydroxyethyl)trimethylammonium or choline salt.

4. The composition of claim 3 wherein the organic nitrogen-containing compound is choline chloride.

5. The composition of claim 1 wherein the inorganic nitrate rest-breaking agent is selected from the group consisting of potassium nitrate, calcium nitrate, ammonium nitrate, calcium ammonium nitrate, urea ammonium nitrate, zinc ammonium nitrate, and mixtures thereof.

6. The composition of claim 5, wherein the inorganic nitrate rest-breaking agent is selected from the group consisting of calcium nitrate, calcium ammonium nitrate, urea ammonium nitrate, and mixtures thereof.

7. The composition of claim 1 wherein the surfactant is an alkoxylated amine or alkoxylated quaternary ammonium compound.

8. The composition of claim 7 wherein the surfactant is an alkoxylated amine.

9. A method for breaking the rest in deciduous fruit species which comprises applying to said species a rest breaking composition of claim 1.

10. The method of claim 9 wherein the deciduous fruit species is selected from the group consisting of apple species and grape species.

11. The method of claim 9 wherein the organic nitrogen-containing compound is selected from the group consisting of (2-hydroxyethyl)tri($C_1$–$C_3$)alkylammonium or choline salts, (2-hydroxypropyl)tri($C_1$–$C_3$)alkylammonium salts, and (2-hydroxybutyl)tri($C_1$–$C_3$)-alkylammonium salts, and mixtures thereof.

12. The method of claim 9 wherein the organic nitrogen-containing compound is a (2-hydroxyethyl)trimethylammonium or choline salt.

13. The method of claim 12 wherein the organic nitrogen-containing compound is choline chloride.

14. The method of claim 9 wherein the inorganic nitrate rest-breaking agent is selected from the group consisting of potassium nitrate, calcium nitrate, ammonium, calcium ammonium nitrate, urea ammonium nitrate, zinc ammonium nitrate, and mixtures thereof.

15. The method of claim 14 wherein the inorganic nitrate rest-breaking agent is selected from the group consisting of calcium nitrate, calcium ammonium nitrate, urea ammonium nitrate, and mixtures thereof.

16. The method of claim 9 wherein the surfactant is an alkoxylated amine or alkoxylated quaternary ammonium compound.

17. The method of claim 16 wherein the surfactant is an alkoxylated amine.

* * * * *